United States Patent
Castinado et al.

(10) Patent No.: US 10,567,961 B2
(45) Date of Patent: Feb. 18, 2020

(54) SYSTEM FOR ELECTROENCEPHALOGRAM PATTERNING RECOGNITION FOR AUTHENTICATION

(71) Applicant: BANK OF AMERICA CORPORATION, Charlotte, NC (US)

(72) Inventors: Joseph Benjamin Castinado, North Glenn, CO (US); Charles Russell Kendall, Snoqualmie, WA (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 50 days.

(21) Appl. No.: 15/802,024

(22) Filed: Nov. 2, 2017

(65) Prior Publication Data

US 2019/0132733 A1    May 2, 2019

(51) Int. Cl.
| | | |
|---|---|---|
| G06F 17/30 | (2006.01) | |
| H04W 12/06 | (2009.01) | |
| G16H 10/60 | (2018.01) | |
| H04L 29/06 | (2006.01) | |

(52) U.S. Cl.
CPC ............ *H04W 12/06* (2013.01); *G16H 10/60* (2018.01); *H04L 63/0861* (2013.01)

(58) Field of Classification Search
CPC .... H04W 12/06; G16H 10/60; H04L 63/0861
USPC .......................................................... 726/7
See application file for complete search history.

(56) References Cited

U.S. PATENT DOCUMENTS

| | | | |
|---|---|---|---|
| 3,848,586 A | 11/1974 | Suzuki et al. | |
| 5,495,853 A | 3/1996 | Yasushi | |
| 5,626,145 A | 5/1997 | Clapp et al. | |
| 5,687,291 A | 11/1997 | Smyth | |
| 6,021,346 A | 2/2000 | Ryu et al. | |
| 6,092,058 A | 7/2000 | Smyth | |
| 6,317,627 B1 | 11/2001 | Ennen et al. | |
| 6,488,617 B1 | 12/2002 | Katz | |
| 6,496,724 B1 | 12/2002 | Levendowski et al. | |
| 6,735,467 B2 | 5/2004 | Wilson | |
| 7,035,685 B2 | 4/2006 | Ryu et al. | |
| 7,299,088 B1 | 11/2007 | Thakor et al. | |
| 8,135,957 B2 | 3/2012 | Dinges et al. | |
| 8,457,595 B2* | 6/2013 | MacInnis | G06F 16/2379 455/410 |
| 9,268,876 B2 | 2/2016 | MacInnis et al. | |
| 9,473,493 B2* | 10/2016 | Jayaraman | A61B 5/04842 |
| 10,154,818 B2* | 12/2018 | Zhang | A61B 5/7246 |

(Continued)

*Primary Examiner* — Amare F Tabor
(74) *Attorney, Agent, or Firm* — Michael A. Springs; Moore & Van Allen PLLC; Nicholas C. Russell

(57) ABSTRACT

Embodiments of the invention are directed to systems, methods, and computer program products for electroencephalogram patterning recognition for user authentication into one or more physical or digital locations. In this way, the system may generate a spectral analysis baseline electroencephalogram reading for a user that can be segmented and analyzed based on a specific time span associated with a known stimulus or event, and diagnostic applications generally focus on either event-related potentials or the like. Upon initiating a request to enter a location requiring authentication, an electroencephalogram reading may be generated and patterned after the baseline electroencephalogram reading for the user. The system may perform patterned recognition of the readings and provide an authentication confidence of the user for authentication into the location.

17 Claims, 7 Drawing Sheets

(56) References Cited

U.S. PATENT DOCUMENTS

| | | | |
|---|---|---|---|
| 10,176,894 B2* | 1/2019 | Park | G16H 20/40 |
| 2004/0077966 A1 | 4/2004 | Yamaguchi et al. | |
| 2004/0077967 A1 | 4/2004 | Jordan | |
| 2005/0085872 A1 | 4/2005 | Yanagihara et al. | |
| 2006/0135879 A1 | 6/2006 | Liley | |
| 2010/0191140 A1 | 7/2010 | Terada et al. | |
| 2010/0317988 A1 | 12/2010 | Terada et al. | |
| 2011/0071416 A1 | 3/2011 | Terada et al. | |
| 2014/0159862 A1 | 6/2014 | Yang et al. | |
| 2014/0178843 A1 | 6/2014 | Smyth | |
| 2015/0081226 A1* | 3/2015 | Baki | A61B 5/0476 702/19 |
| 2015/0294085 A1* | 10/2015 | Kare | G16H 10/60 705/3 |
| 2016/0004862 A1 | 1/2016 | Almehmad et al. | |
| 2016/0183812 A1 | 6/2016 | Zhang et al. | |
| 2016/0188839 A1* | 6/2016 | Kaul | G06F 19/3456 705/2 |
| 2017/0118204 A1* | 4/2017 | Laine | A61B 5/01 |
| 2017/0196501 A1* | 7/2017 | Watson | G16H 10/60 |
| 2017/0228512 A1* | 8/2017 | Driscoll | G06F 19/3418 |
| 2017/0323073 A1* | 11/2017 | Westermann | G06F 19/3418 |

* cited by examiner

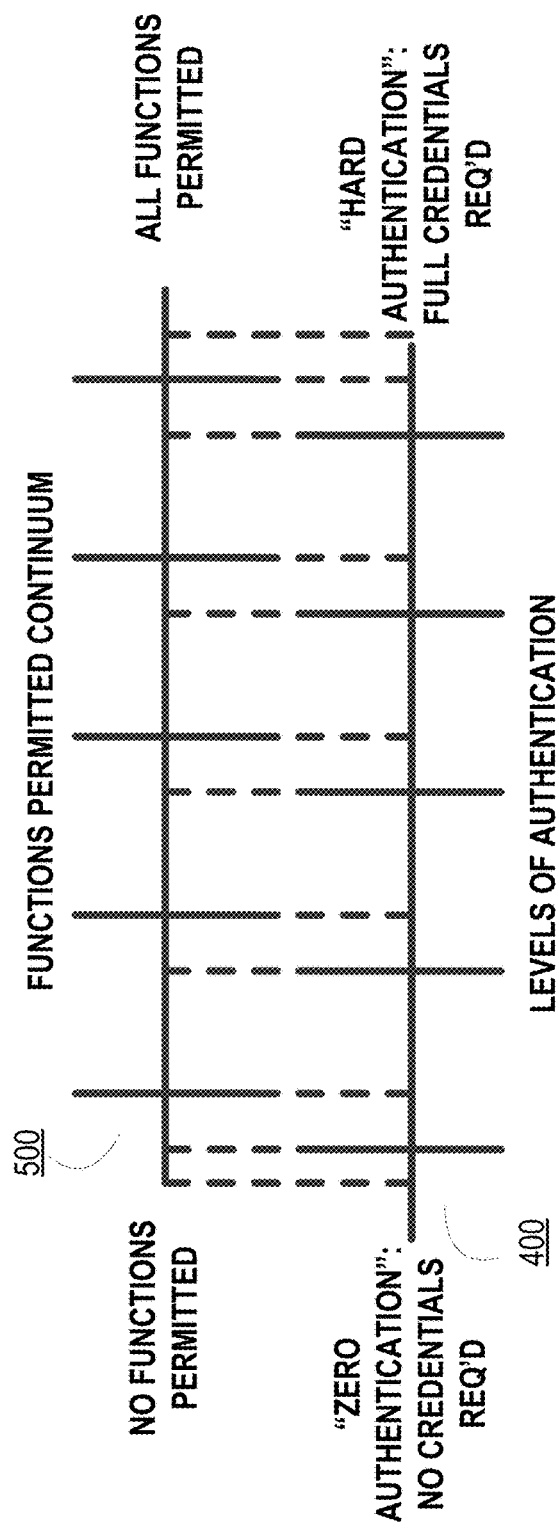

SYSTEM FOR ELECTROENCEPHALOGRAM PATTERNING RECOGNITION FOR AUTHENTICATION

BACKGROUND

With advancements in technology, use of electroencephalography (EEG) and access to EEG devices are becoming more prevalent.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

In some embodiments, the invention utilizes EEG data to identify a user and allow authentication and validation of the user for secure access to one or more locations. In this way, the invention generates a baseline EEG user profile that contains the user EEG profile including user EEG reactions to stimuli and the like. As such, the EEG data can be segmented and analyzed based on a specific time span associated with a known stimulus or event, and diagnostic applications generally focus on either event-related potentials (ERPs), some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). The invention may determining what component frequencies are present in a specific user EEG response may involve computing a Fourier transform of a sampled user EEG signal. One can then resynthesize the sampled user EEG signal or compare subsequent signal analysis to detect similarities.

In some embodiments, the invention may also relate to an averaged ERP to provide accurate biometric information. One such method, cognitive event-related biometric recognition (CEREBRE) protocol allows for 100% identification accuracy utilizing individually unique responses from multiple functional brain systems, such as the primary visual, facial recognition, and gustatory/appetitive systems.

Some embodiments of the invention may incorporate such methods in order to identify users with a high degree of accuracy, and may associate this identification information with a user profile to identify the user and authentication the user into secure locations.

Embodiments of the invention relate to systems, methods, and computer program products for EEG patterning recognition for authentication, the invention comprising: identifying a transmission from an EEG reader for establishing a baseline EEG reading for the user; storing the baseline EEG reading for the user in a EEG profile for the user, wherein the EEG profile comprises the baseline EEG reading for the user and authentication codes for one or more authentication locations; identifying the user requesting authentication into the one or more authentication locations; locating an EEG reader at the one or more authentication locations and form a communicable linkage with the EEG reader at the one or more authentication locations; receiving an EEG reading from the EEG reader at the one or more authentication locations; performing comparative spectral analysis to the EEG reading to identify a match or partial match to the baseline EEG reading for the user; and allowing access into the one or more authentication locations based on a confidence of the comparative spectral analysis.

In some embodiments, establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

In some embodiments, receiving an EEG reading from the EEG reader at the one or more authentication locations, further comprises transmitting a request via the communicable linkage for generation of the EEG reading from the EEG reader at the one or more authentication locations.

In some embodiments, establishing a baseline EEG reading for the user further comprises transmitting one or more known stimuli to the user for EEG reading of user reaction to the known stimuli.

In some embodiments, allowing access into the one or more authentication locations based on a confidence of the comparative spectral analysis further comprises allowing access to functions of a portion of the authentication locations based on the confidence of a match of the EEG reading to the baseline EEG reading for the user to a hard authentication and an incomplete match of the EEG reading to the baseline EEG reading for the user to a soft authentication.

In some embodiments, performing comparative spectral analysis to the EEG reading to identify a match or partial match to the baseline EEG reading for the user further comprises generating a confidence that the EEG reading is an EEG reading of the user based on a comparative analysis to the baseline EEG reading for the user.

In some embodiments, one or more authentication locations comprise physical or digital locations requiring the user to authenticate to gain access to at least a portion of the physical or digital locations.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
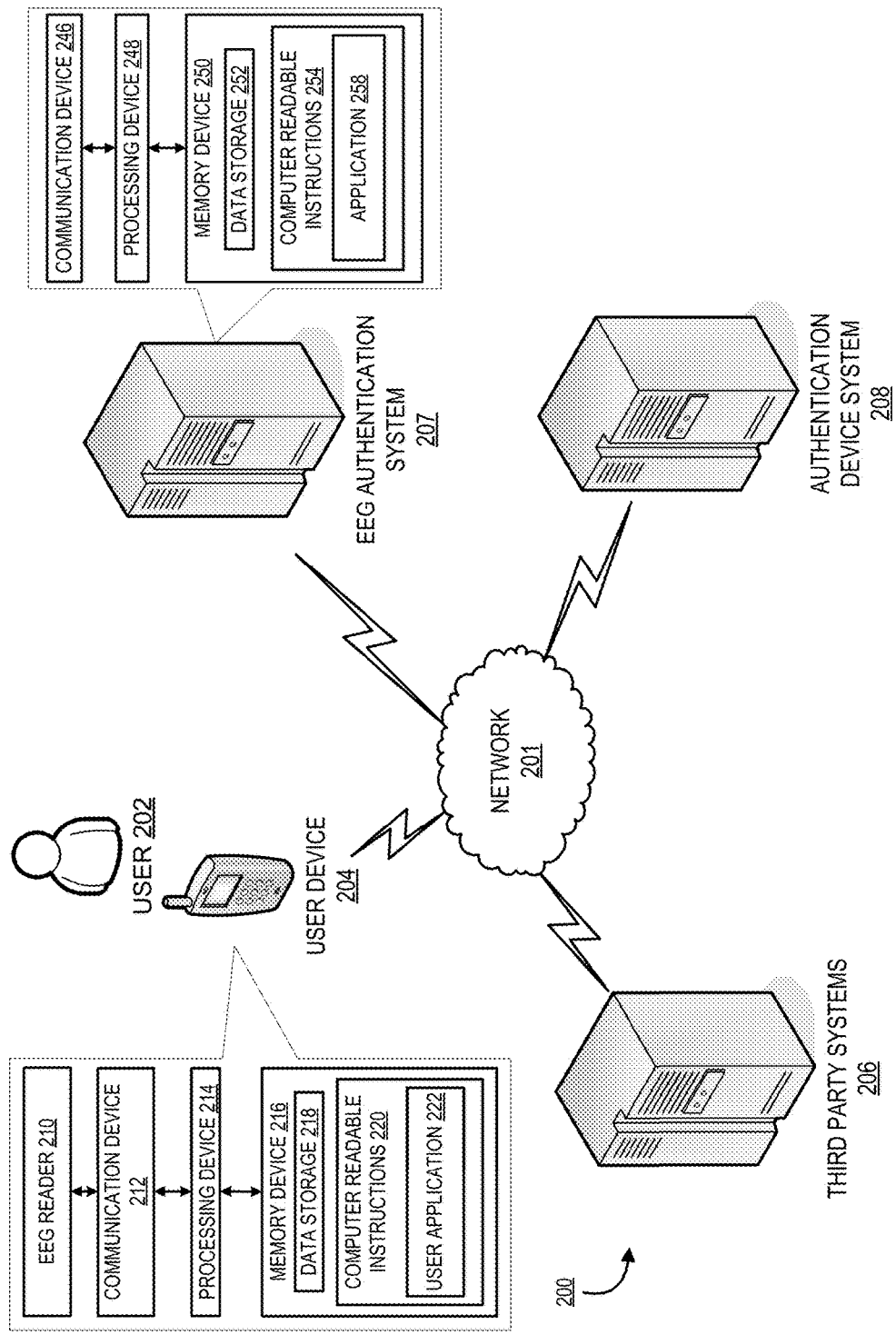
Figure 2:
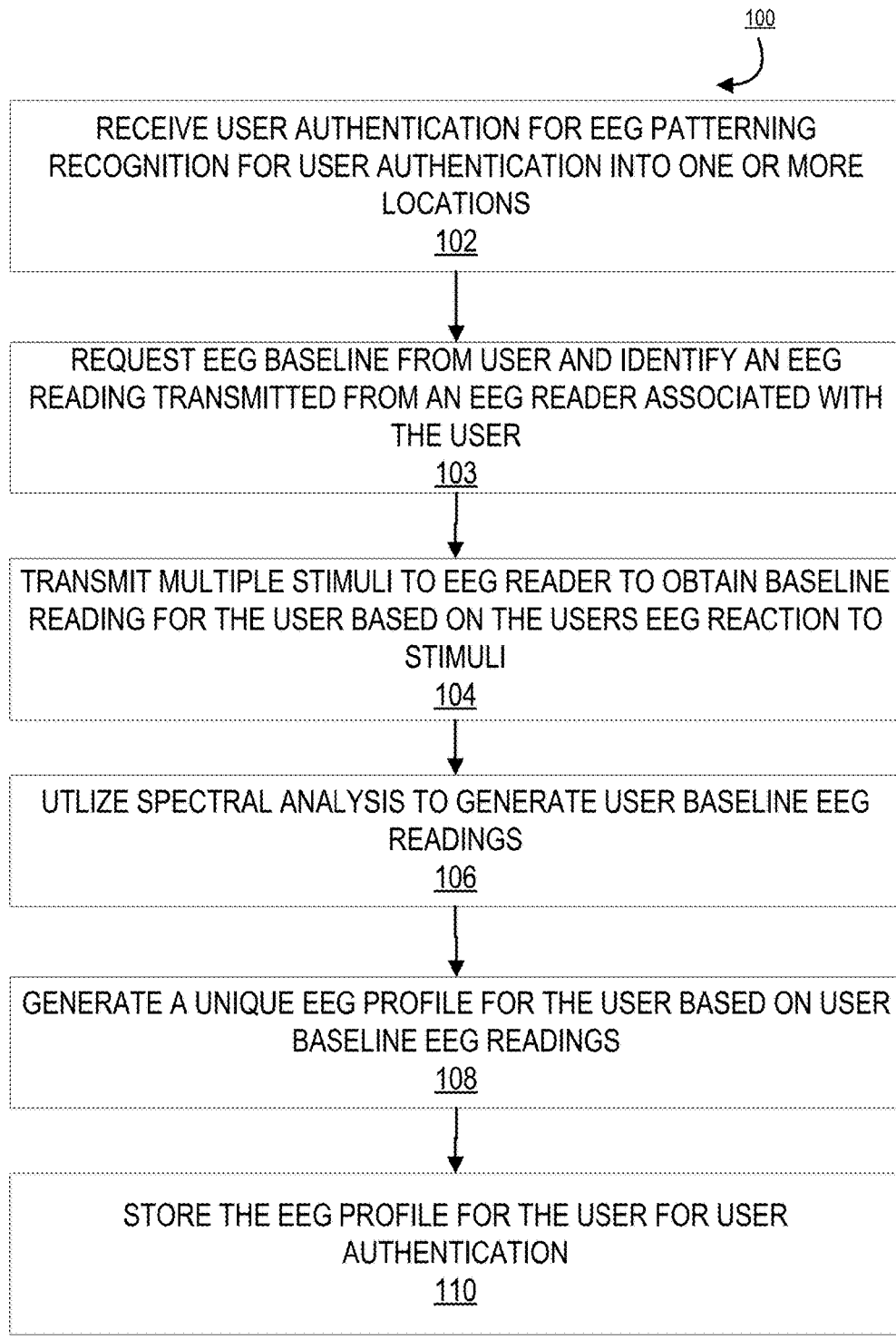
Figure 3:
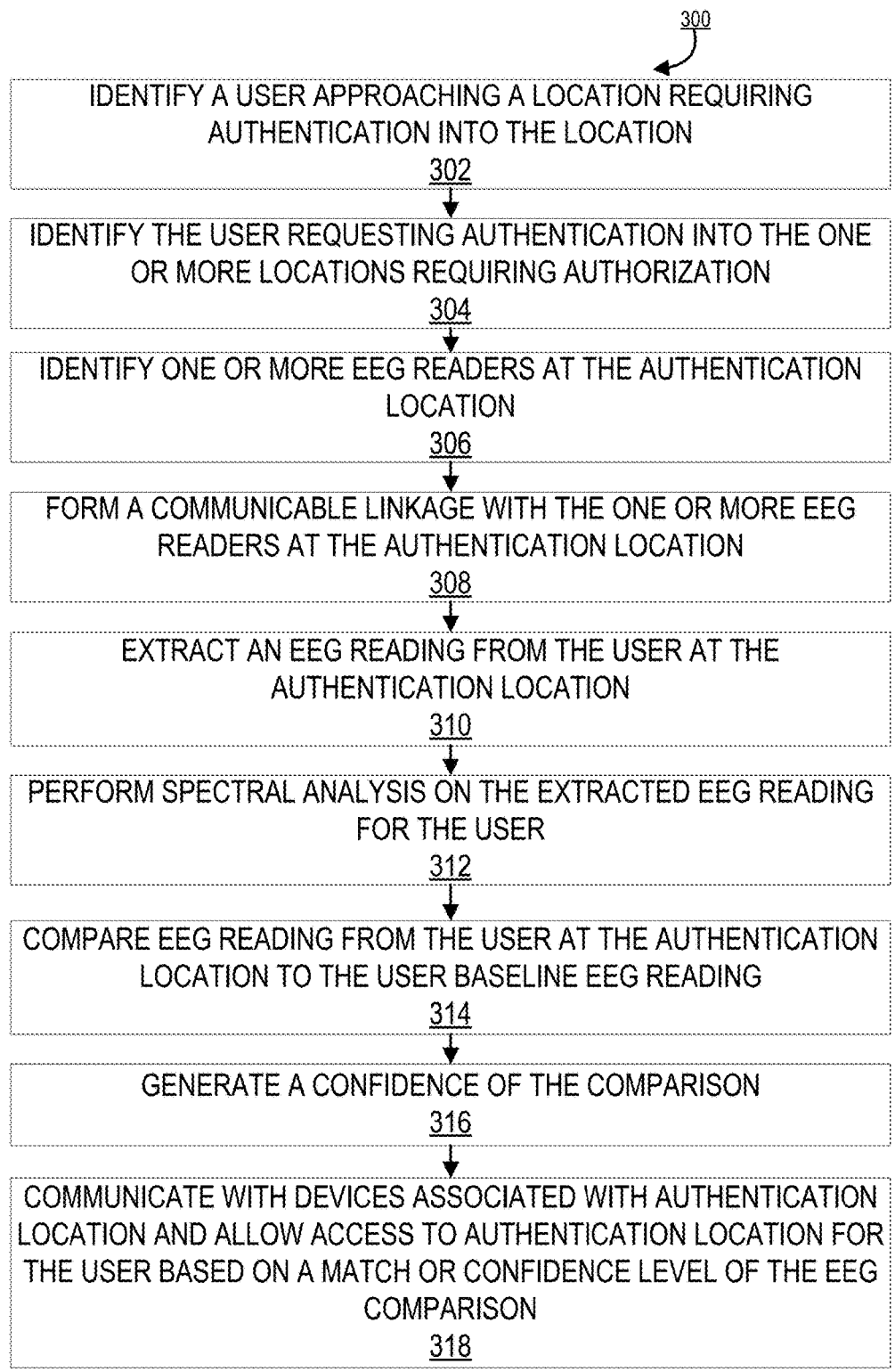
Figure 4A:
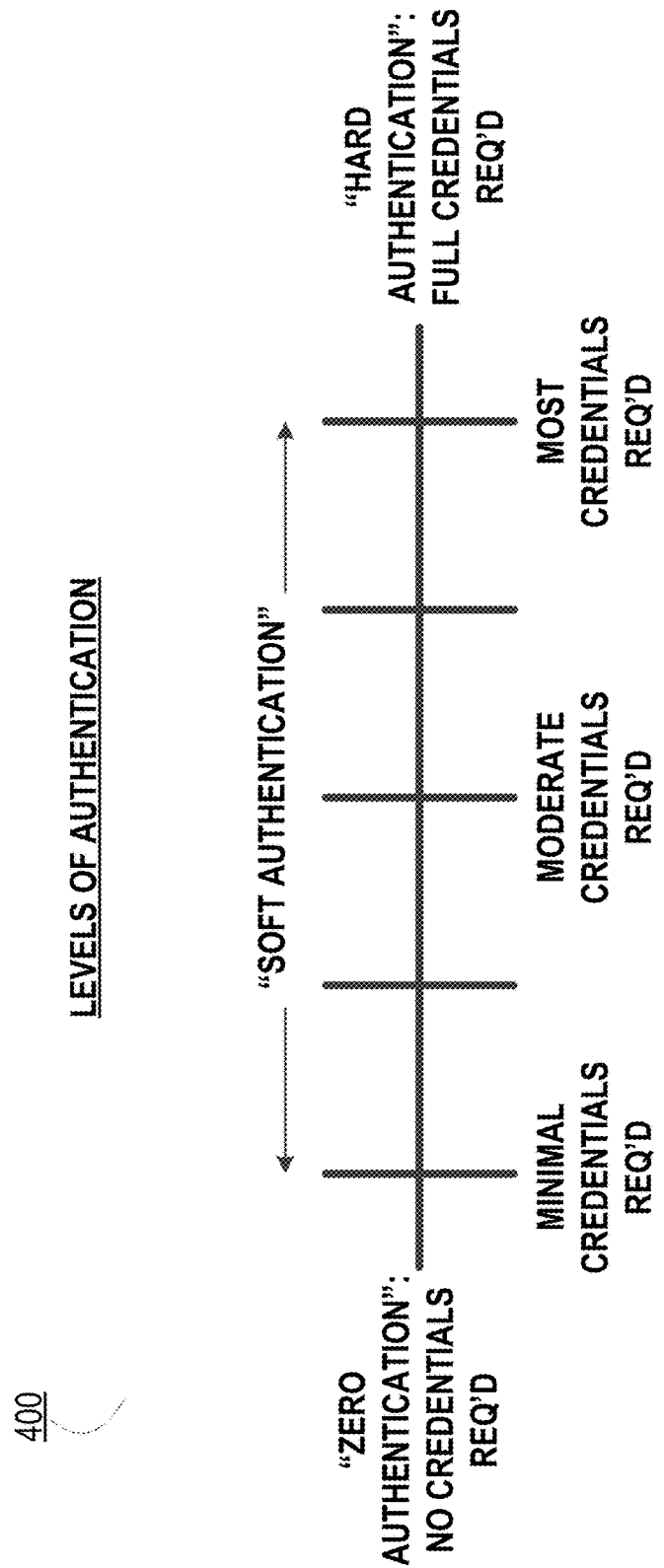
Figure 4B:
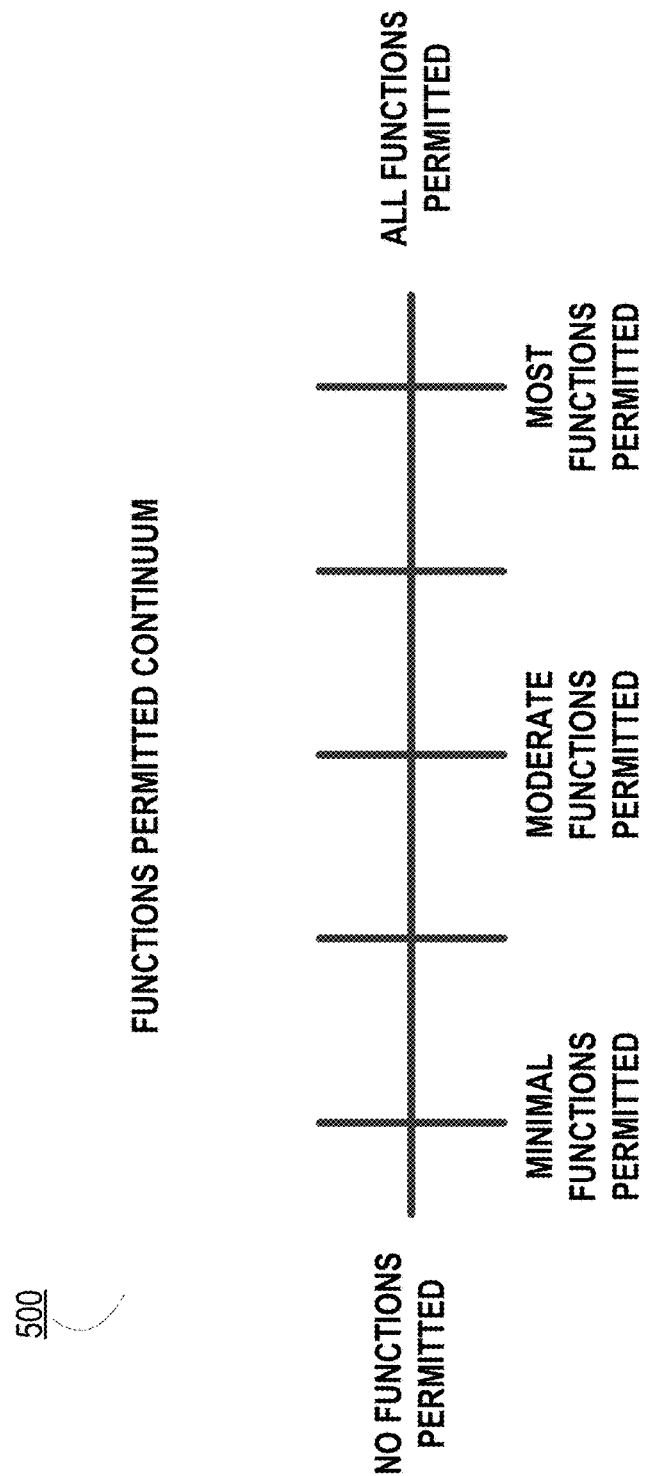
Figure 4D:
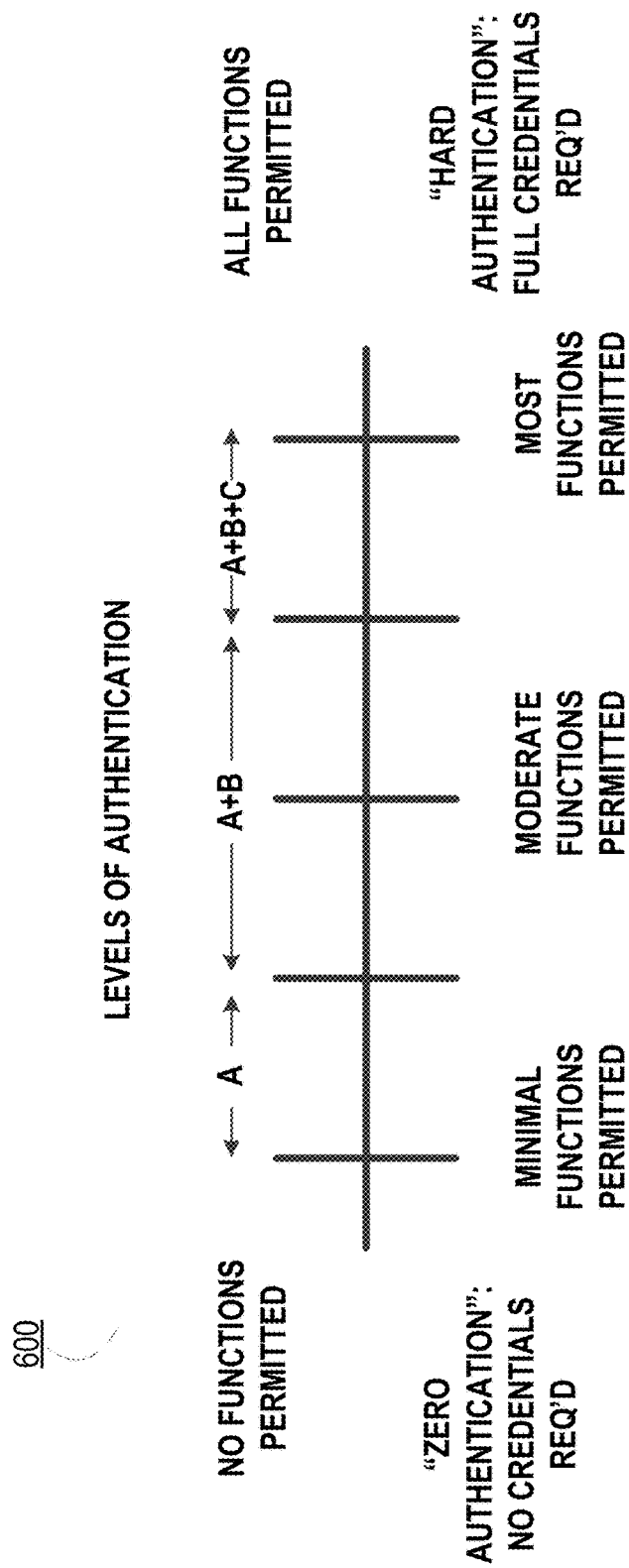

Having thus described embodiments of the invention in general terms, reference will now be made to the accompanying drawings, where:

FIG. 1 illustrates an EEG pattern recognition system environment, in accordance with embodiments of the present invention;

FIG. 2 illustrates a high level flowchart for EEG patterning recognition for authentication processing, in accordance with embodiments of the present invention;

FIG. 3 illustrates a flow chart for EEG patterning recognition for authentication, in accordance with embodiments of the present invention;

FIG. 4A illustrates an authentication continuum for the EEG patterning recognition authentication processing, in accordance with embodiments of the present invention;

FIG. 4B illustrates an authentication continuum for the EEG patterning recognition authentication processing, in accordance with embodiments of the present invention;

FIG. 4C illustrates an authentication continuum for the EEG patterning recognition authentication processing, in accordance with embodiments of the present invention; and FIG. 4D illustrates an authentication continuum for the EEG patterning recognition authentication processing, in accordance with embodiments of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

In some embodiments, an "entity" may be a financial institution or third party merchant. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. An "account" may be the relationship that the user has with the entity. Examples of accounts include a deposit account, such as a transactional account (e.g., a banking account), a savings account, an investment account, a money market account, a time deposit, a demand deposit, a pre-paid account, a credit account, a non-monetary user profile that includes only personal information associated with the user, or the like. The account is associated with and/or maintained by the entity. In other embodiments, an entity may not be a financial institution. In still other embodiments, the entity may be the merchant itself.

A "transaction" or "resource distribution" refers to any communication between a user and the financial institution or other entity monitoring the user's activities to transfer funds for the purchasing or selling of a product. A transaction may refer to a purchase of goods or services, a return of goods or services, a payment transaction, a credit transaction, or other interaction involving a user's account. In the context of a financial institution, a transaction may refer to one or more of: a sale of goods and/or services, initiating an automated teller machine (ATM) or online banking session, an account balance inquiry, a rewards transfer, an account money transfer or withdrawal, opening a bank application on a user's computer or mobile device, a user accessing their e-wallet, or any other interaction involving the user and/or the user's device that is detectable by the financial institution. A transaction may include one or more of the following: renting, selling, and/or leasing goods and/or services (e.g., groceries, stamps, tickets, DVDs, vending machine items, and the like); making payments to creditors (e.g., paying monthly bills; paying federal, state, and/or local taxes; and the like); sending remittances; loading money onto stored value cards (SVCs) and/or prepaid cards; donating to charities; and/or the like. In some embodiments, the invention may authorize or allow a user access to one or more websites, physical locations, secure locations, accounts, interfaces, or the like.

In some embodiments, the invention associated with an electroencephalogram (EEG) which is an electrophysiological monitoring method to record electrical activity of the brain. EEG measures voltage fluctuations resulting from ionic current with neurons of the brain. In this way, the EEG refers to the recording of the brain's electrical activity over a period of time. In some embodiments, an EEG may be used to identify a user based on tracking the EEG of the user and generating a baseline EEG for the user. This may be used to identify the user for authentication of the user and access to one or more authentication required locations.

In some embodiments, the invention uses electroencephalography resources to authorize and authenticate a user. In this way, the invention interconnects with a network for real-time data transfer from user devices, third party devices, and other connected devices to receive, analyze, and react to electroencephalography data. As such, upon receiving and analyzing specific user based electroencephalography data, the system may form and activate a user specific electroencephalography profile and send control signals across a network for user authentication.

In some embodiments, the invention utilizes a brain computer interface (BCI), or a direct communication pathway between an enhanced or wired brain and an external device. EEG is an electrophysiological monitoring method to record electrical activity of the brain, and is one of the most studied non-invasive approaches to brain computer interfacing, mainly due to its fine temporal resolution, ease of use, portability, and low set-up cost. Typically completely non-invasive, existing EEG technology may involve placing a number of electrodes along the scalp to measure voltage fluctuations resulting from ionic current within the neurons of the brain; however, modern research indicates that EEG devices may become smaller, more portable and easier to use, and embodiments of the present invention contemplate the use of such "wearable EEG" electronics which utilize a low power wireless connection and "dry" electrodes which are characterized by their lack of need for conductive gel during use.

EEG data can be segmented and analyzed based on a specific time span associated with a known stimulus or event, and diagnostic applications generally focus on either event-related potentials (ERPs), some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). Spectral analysis is a method for the study of EEG signals, and specifically involves the study of neural oscillations, more commonly known as brain waves, that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

EEG measures voltage fluctuations resulting from ionic current within the neurons of the brain, and in clinical contexts, EEG refers to the recording of the brain's spontaneous electrical activity over a period of time. EEG has very high temporal resolution, on the order of milliseconds, and EEG signals are commonly recorded at sampling rates between 250 and 2000 Hz in clinical and research settings, while modern EEG data collection systems are capable of recording at sampling rates even above 20,000 Hz if so desired. EEG is relatively tolerant of subject movement, unlike most other neuroimaging techniques, and operation of EEG devices is silent, allowing for study of responses to auditory stimuli without the introduction of noise into the EEG signal. Detection of cover brain processing is possible with EEG, meaning that processing does not require a physical response to be registered by an EEG system and allowing for the use of EEG by users who are incapable of making a motor response.

One variation of ERP, known as the P300 response is characterized as a "late" potential, as it occurs at 300-800 milliseconds after the associated stimulus, and it is also known as the P3, N2-P3 complex, P3a and P3b, late positive complex, and LPC. P300, refers to the electrically positive character of the response as well as the latency of greater than or equal to 300 milliseconds. The P300 may either be a unitary response or a part of a larger grouping of several responses such as the memory and encoding related multi-faceted electroencephalographic response, or P300-MERMER. Embodiments of the present invention utilizes one or more of these responses in order to establish an objective method of brain fingerprinting, wherein brain responses to known stimuli are detected, quantified, and analyzed to determine whether or not a user knows critical information. Brain fingerprinting systems are able to compute, with a statistical confidence of 99.9%, a determination of whether or not a user knows critical information presented.

In some embodiments, the invention may also relate to an averaged ERP to provide accurate biometric information. One such method, cognitive event-related biometric recognition (CEREBRE) protocol allows for 100% identification accuracy utilizing individually unique responses from multiple functional brain systems, such as the primary visual, facial recognition, and gustatory/appetitive systems. These results indicate a method of user identification of users via the collection and analysis of EEG readings. Some embodiments of the invention may incorporate such methods in order to identify users with a high degree of accuracy, and may associate this identification information with a larger profile on the user that contains stored user preferences and demographics. The combined use of the P300 type response analysis, CEREBRE protocol biometric information, and stored user preference and user demographic information allows embodiments of the invention to build a complete picture of who the user is, what they know, what they prefer, and how they are reacting in real-time. The system may react to this known user information according to a set protocol or operator instructions to authorize a user for access to one or more locations.

FIG. 1 illustrates an EEG pattern recognition system environment 200, in accordance with embodiments of the present invention. FIG. 1 provides the system environment 200 for which the distributive network system with specialized data feeds for EEG pattern recognition and authentication based on the EEG pattern recognition. FIG. 1 provides a unique system that includes specialized servers and system communicably linked across a distributive network of nodes required to perform the functions of EEG pattern recognition for real-time authentication of a user.

As illustrated in FIG. 1, the authentication device system 208 is operatively coupled, via a network 201 to the user device 204, EEG authentication system 207, and to the third party systems 206. In this way, the authentication device system 208 can send information to and receive information from the user device 204, EEG authentication system 207, and the third party systems 206. FIG. 1 illustrates only one example of an embodiment of the system environment 200, and it will be appreciated that in other embodiments one or more of the systems, devices, or servers may be combined into a single system, device, or server, or be made up of multiple systems, devices, or servers.

The network 201 may be a system specific distributive network receiving and distributing specific network feeds and identifying specific network associated triggers. The network 201 may also be a global area network (GAN), such as the Internet, a wide area network (WAN), a local area network (LAN), or any other type of network or combination of networks. The network 201 may provide for wireline, wireless, or a combination wireline and wireless communication between devices on the network 201.

In some embodiments, the user 202 is one or more individuals authenticating into an account, device, system, network, or the like. The user may have one or more accounts associated with resources for distribution of the resources. FIG. 1 also illustrates a user device 204. The user device 204 may be, for example, a desktop personal computer, business computer, business system, business server, business network, a mobile system, such as a cellular phone, smart phone, personal data assistant (PDA), laptop, or the like. The user device 204 generally comprises a communication device 212, a processing device 214, and a memory device 216. The processing device 214 is operatively coupled to the communication device 212 and the memory device 216. The processing device 214 uses the communication device 212 to communicate with the network 201 and other devices on the network 201, such as, but not limited to the third party systems 206, the authentication device system 208, and the EEG authentication system 207. As such, the communication device 212 generally comprises a modem, server, or other device for communicating with other devices on the network 201.

The user device 204 comprises computer-readable instructions 220 and data storage 218 stored in the memory device 216, which in one embodiment includes the computer-readable instructions 220 of a user application 222. In some embodiments, the user application 222 allows a user 202 to set up marker codes and communicate with the third party systems 206.

Furthermore, the user device 204 may comprise an EEG reader 210. An EEG reader 210 is an electrophysiological monitoring method to record electrical activity of the brain. EEG measures voltage fluctuations resulting from ionic current with neurons of the brain. In this way, the EEG refers to the recording of the brain's electrical activity over a period of time. In some embodiments, an EEG may be used to identify a user based on tracking the EEG of the user and generating a baseline EEG for the user. This may be used to identify the user for authentication of the user and access to one or more authentication required locations.

As further illustrated in FIG. 1, the EEG authentication system 207 generally comprises a communication device 246, a processing device 248, and a memory device 250. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 248 is operatively coupled to the communication device 246 and the memory device 250. The processing device 248 uses the communication device 246 to communicate with the network 201 and other devices on the network 201, such as, but not limited to the authentication device system 208, the third party systems 206, and the user device 204. As such, the communication device 246 generally comprises a modem, server, or other device for communicating with other devices on the network 201.

As further illustrated in FIG. 1, the EEG authentication system 207 comprises computer-readable instructions 254 stored in the memory device 250, which in one embodiment includes the computer-readable instructions 254 of an application 258. In some embodiments, the memory device 250 includes data storage 252 for storing data related to the system environment 200, but not limited to data created and/or used by the application 258.

In one embodiment of the EEG authentication system 207 the memory device 250 stores an application 258. Furthermore, the EEG authentication system 207, using the processing device 248 codes certain communication functions described herein. In one embodiment, the computer-executable program code of an application associated with the application 258 may also instruct the processing device 248 to perform certain logic, data processing, and data storing functions of the application. The processing device 248 is configured to use the communication device 246 to communicate with and ascertain data from one or more authentication device system 208, EEG authentication system 207, and/or user device 204.

In some embodiments, the EEG authentication system 207 may analyze via spectral analysis or the like EEG data provided by one or more systems on the network and/or generated by the EEG authentication system 207. In this way, the EEG authentication system 207 may segment and analyze EEG data based on a specific time span associated with a known stimulus or event, and diagnostic applications generally focus on either event-related potentials (ERPs), some variation thereof, or on the spectral content of EEG.

In some embodiments, the EEG authentication system 207 may utilize ERP such as a P300 response that occurs at 300-800 milliseconds after the associated stimulus that identifies electrically positive character of the response as well as the latency of greater than or equal to 300 milliseconds. In some embodiments, the EEG authentication system 207 may utilize one or more of these responses in order to establish an objective method of brain fingerprinting, wherein brain responses to known stimuli are detected, quantified, and analyzed to determine whether or not a user knows critical information. Brain fingerprinting systems are able to compute, with a statistical confidence of 99.9%, a determination of whether or not a user knows critical information presented.

In other embodiments, the EEG authentication system 207 may average ERP to provide accurate biometric information. In this way, the EEG authentication system 207 may utilize cognitive event-related biometric recognition (CEREBRE) protocol for identification accuracy utilizing individually unique responses from multiple functional brain systems, such as the primary visual, facial recognition, and gustatory/appetitive systems. These results indicate a method of user identification of users via the collection and analysis of EEG readings. Some embodiments of the EEG authentication system 207 may incorporate such methods in order to identify users with a high degree of accuracy, and may associate this identification information with a larger profile on the user that contains stored user preferences and demographics. The combined use of the P300 type response analysis, CEREBRE protocol biometric information, and stored user preference and user demographic information allows the EEG authentication system 207 to build a complete picture of who the user is, what they know, what they prefer, and how they are reacting in real-time. The system may react to this known user information according to a set protocol or operator instructions to modify the user's experience based on a number of factors depending on the capabilities of the user device, third party device, or smart device with which the system is interfacing As illustrated in FIG. 1, the third party systems 206 is connected to the authentication device system 208, user device 204, and EEG authentication system 207. The third party systems 206 has the same or similar components as described above with respect to the user device 204 and the EEG authentication system 207. In some embodiments, the third party systems 206 may further include an EEG reader. While only one third party system 206 is illustrated in FIG. 1, it is understood that multiple authentication device system 208 may make up the system environment 200.

As illustrated in FIG. 1, the authentication device system 208 is connected to the EEG authentication system 207, user device 204, and third party systems 206. In other embodiments, the authentication device system 208 may be a third party system separate from the EEG authentication system 207. The authentication device system 208 has the same or similar components as described above with respect to the user device 204 and the third party systems 206. While only one authentication device system 208 is illustrated in FIG. 1, it is understood that multiple authentication device system 208 may make up the system environment 200. In some embodiments, the authentication device system 208 may further include an EEG reader.

In some embodiments, an EEG reader while illustrated with the user device 204 may also be associated with the third party systems 206, the EEG authentication system 207, and/or the authentication device system 208. The EEG reader is an electrophysiological monitoring method to record electrical activity of the brain.

It is understood that the servers, systems, and devices described herein illustrate one embodiment of the invention. It is further understood that one or more of the servers, systems, and devices can be combined in other embodiments and still function in the same or similar way as the embodiments described herein. The authentication device system 208 may generally include a processing device communicably coupled to devices as a memory device, output devices, input devices, a network interface, a power source, one or more chips, and the like. The authentication device system 208 may also include a memory device operatively coupled to the processing device. As used herein, memory may include any computer readable medium configured to store data, code, or other information. The memory device may include volatile memory, such as volatile Random Access Memory (RAM) including a cache area for the temporary storage of data. The memory device may also include non-volatile memory, which can be embedded and/ or may be removable. The non-volatile memory may additionally or alternatively include an electrically erasable programmable read-only memory (EEPROM), flash memory or the like. The memory device may store any of a number of applications or programs which comprise computer-executable instructions/code executed by the processing device to implement the functions of the authentication device system 208 described herein.

FIG. 2 illustrates a high level flowchart for EEG patterning recognition for authentication processing 100, in accordance with embodiments of the present invention. As illustrated in block 102, the process 100 is initiated by receiving user authentication for EEG patterning recognition for user authentication into one or more locations. These locations may include a website, server, platform, physical location, or the like that requires authentication or authentication to gain access to one or more portions of the location. In this way, the user is requesting for the system for EEG patterning recognition for authentication of the user.

Upon receiving the request, the system may further request an EEG baseline from the user. As illustrated in block 103, upon request for an EEG baseline from the user, the system may identify an EEG reading transmitted from an EEG reader associated with the user.

In this way, the system may utilize a brain computer interface (BCI), or a direct communication pathway between an enhanced or wired brain and an external device such as the EEG reader or user device. EEG is an electrophysiological monitoring method to record electrical activity of the brain, and is a non-invasive approaches to brain computer interfacing, mainly due to its fine temporal resolution, ease of use, portability, and low set-up cost. EEG devices may be small portable and easier to use devices such as a wearable EEG device or EEG reader which utilize a low power wireless connection and dry electrodes which are characterized by their lack of need for conductive gel during use. These may be utilized by the user to determine a baseline EEG reading for the user.

The EEG data can be segmented and analyzed based on a specific time span associated with a known stimulus or event, and diagnostic applications generally focus on either ERPs, some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). In some embodiments, the invention may use spectral analysis as a method for the study of EEG signals, which specifically involves the study of neural oscillations, more commonly known as "brain waves," that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP that the invention may involve is known as the P300 response. The P300 is characterized as a late potential, as it occurs at 300-800 milliseconds after the associated stimulus, and it is also known to those skilled in the art as the P3, N2-P3 complex, P3a and P3b, late positive complex, and LPC. P300 may either be a unitary response or a part of a larger grouping of several responses. Embodiments of the present invention may relate to a system that utilizes one or more of these responses in order to establish an objective method of brain fingerprinting, wherein brain responses to known stimuli are detected, quantified, and analyzed to determine whether or not a user has knowledge of critical information. Brain fingerprinting systems are able to compute a statistical confident determination of whether or not a user knows critical information presented.

Embodiments of the present invention may also utilize an averaged ERP to provide accurate biometric information and generate an EEG baseline for the user. One such method, known as the cognitive event-related biometric recognition (CEREBRE) protocol, utilizes individually unique responses from multiple functional brain systems, such as the primary visual, facial recognition, and gustatory/appetitive systems to generate unique EEG readings for a user. These results indicate a feasible method of user identification of users via the collection and analysis of EEG readings. Some embodiments of the invention may incorporate such methods in order to identify users with a high degree of accuracy, and may associate this identification information with a larger profile on the user that contains stored user preferences and demographics.

In some embodiments, the system may utilize a combined use of the P300 type response analysis, CEREBRE protocol biometric information, and stored user preferences to build an EEG baseline of the user.

As illustrated in block 104, the process 100 continues by transmitting multiple stimuli to the EEG reader to obtain the baseline reading for the user. These stimuli may include colors, pictures, videos, or the like and record the EEG readings from the user visualizing the one or more stimuli. As illustrated in block 106, the process 100 continues by utilizing spectral analysis to generate user baseline EEG readings. In some embodiments, the invention generates a user specific EEG profile in a user profile repository using EEG data collected from a user device containing an EEG reader. The user specific EEG profile includes the user EEG baseline. User specific EEG profile data is collected via a network and stored as a database of event-related potentials or evoked potentials corresponding to specific sets of stimuli, events, or triggers.

In this way, the invention interconnects with a network for real-time data transfer from user devices, third party devices, and other connected devices to receive, analyze, and react to EEG data from an EEG reader to allow generation of a determined user status within a user network account to trigger modification and management of a user experience based on real time EEG data and user specific EEG profile data. In some embodiments, the user status may not be formally known to the user and may only be enacted when an institution confirms an external event is occurring or stimulus is present. When the status is enabled, the system may form and activate a first control signal to cause the EEG reader to capture subsequent EEG readings and react accordingly.

The system may further develop the user specific EEG profile corresponding to the user by analyzing predetermined attributes of the subsequent EEG signals and storing them as event-related potentials or evoked-potentials known to be associated with a particular user response. Analysis of the predetermined attributes of subsequent EEG readings may also allow the system to determine a user response based on a similarity between the analysis results and the same predetermined attributes for a known response. In this way, information received from the EEG reader can be used to determine when the user is present at a certain location, third party system, smart system, or other connected user device, and the subsequent EEG signals can be further analyzed against prior recorded event-related potentials to determine other attributes of the user's experience.

As illustrated in block 108, the user EEG profile may be generated based on the baseline EEG readings. Finally, as illustrated in block 110, the process 100 is completed upon storing the EEG profile for the user for user authentication. In some embodiments, the storage is preformed cryptographically and/or encrypted, such that multiple security levels exist around the EEG profile for user privacy protection.

FIG. 3 illustrates a flow chart for EEG patterning recognition for authentication 300, in accordance with embodiments of the present invention. As illustrated in block 302, the process 300 is initiated by identifying a user approaching a location requiring authentication from the user into the location. In some embodiments, a location may be a physical location, a website, a server, or the like. Approaching the location may be accessing a sign in page, approaching a physical location requiring authentication for access, or the like.

Next, as illustrated in block 304, the process 300 continues by identifying that the user is requesting authentication into the one or more locations requiring authentication. In some embodiments, the user may access a homepage on a website that requires authentication for access to additional content. In some embodiments, the user may be performing a financial transaction and require authentication of the user to complete the transaction. In other embodiments the user may be at a physical location attempting to gain access to a physical location that requires authentication to access and enter. The system may identify the user requesting authentication into the one or more locations requiring authentication by third party system communication, user communication, or the like.

As illustrated in block 306, the process 300 continues by identifying one or more EEG readers at the authentication location. In some embodiments, the EEG reader may be associated with the authentication location, such as an EEG reader integrated within a third party system, or the like. In some embodiments, the EEG reader may be a remote reader that is portable at the location. In some embodiments, the EEG reader may be associated with the user device.

The system may then form a communicable linkage with the one or more EEG readers identified at the authentication location, as illustrated in block 308. In this way, the system may integrate into the one or more EEG readers at the authentication location in order to activate and perform an EEG reading on the user. As illustrated in block 310, the process 100 continues by extracting an EEG reading for the user at the authentication location using the one or more EEG readers at the authentication location.

Next, as illustrated in block 312, the process 300 continues by performing spectral analysis on the extracted EEG reading for the user. As discussed, the EEG reading data can be segmented and analyzed based on a specific time span associated with a known stimulus or event, and diagnostic applications generally focus on either ERPs, some variation thereof, or on the spectral content of EEG. Data that is time-locked to complex processing of various stimuli may be referred to as an event-related potential, while a subclass of the EEG technique also include evoked potentials, or time-locked averages of EEG activity associated with presentation of a specific stimulus of some sort (auditory, visual, or somatosensory). Spectral analysis is a method for the study of EEG signals, and specifically involves the study of neural oscillations, more commonly known as brain waves, that can be observed in EEG signals in the frequency domain. Through statistical analysis and signal processing, the frequency content of EEG signals can be characterized, and periodicities can be detected in the data by observing peaks at the sequences corresponding to these periodicities. Determining what component frequencies are present in a specific user EEG response may involve computing a Fourier transform of a sampled user EEG signal. One can then resynthesize the sampled user EEG signal or compare subsequent signal analysis to detect similarities.

One variation of ERP, known as the P300 response is characterized as a late potential, as it occurs at 300-800 milliseconds after the associated stimulus, and it is also known as the P3, N2-P3 complex, P3a and P3b, late positive complex, and LPC. P300, refers to the electrically positive character of the response as well as the latency of greater than or equal to 300 milliseconds. The P300 may either be a unitary response or a part of a larger grouping of several responses such as the memory and encoding related multifaceted electroencephalographic response, or P300-MERMER.

In some embodiments, the spectral analysis may also refer to an averaged ERP to provide accurate biometric information. One such method, cognitive event-related biometric recognition (CEREBRE) protocol is utilized for individually unique responses from multiple functional brain systems, such as the primary visual, facial recognition, and gustatory/appetitive systems. These results indicate a method of user identification of users via the collection and analysis of EEG readings. Some embodiments of the invention may incorporate such methods in order to identify users with a high degree of accuracy, and may associate this identification information with a larger profile on the user that contains stored user preferences and demographics Next, as illustrated in block 314, the system may compare the EEG reading from the user at the authentication location to the user baseline EEG reading. In this way, the system may compare the baseline EEG reading to the user EEG reading at the authentication location. The baseline EEG reading may have one or more variations due to various stimuli being introduced to the user during generation of the baseline EEG reading. The combined use of the P300 type response analysis, CEREBRE protocol biometric information, and stored user preference determine if a confidence match between the baseline EEG reading of the user and the EEG reading of the user at the authentication location.

As illustrated in block 316, the process 300 continues to generate a confidence in the comparison of the user baseline EEG reading to the EEG reading at the authentication location. The confidence may generate a level of authentication acceptable by the EEG reading. In some embodiments, the confidence may determine that only a soft authentication location may be accessed using the EEG reading. In other embodiments, the confidence may determine that a hard authentication location may be accessed using the EEG reading.

Finally, as illustrated in block 318, the process 300 is completed upon system communication with the devices associated with the authentication location and allow access to the authentication location for the user based on a match or confidence level of the EEG comparison. In some embodiments, the system may also utilize other biometric means for confirmation of confidence of the EEG match, such as heart rate, blood pressure, and the like to identify the tolerance or confidence the system has with the user being authenticated into the authentication location.

FIG. 4A illustrates an authentication continuum for the EEG patterning recognition authentication processing 400, in accordance with embodiments of the present invention. On the left-hand side of the continuum, a "zero authentication" requires no authentication credentials. On the right-hand side of the continuum, a "hard authentication" requires full authentication credentials. This means that it requires the strictest combination of credentials. In between the two extremes, "a soft authentication" requires minimal credentials, moderate credentials or most credentials for various points along the continuum. The continuum generally represents the number of credentials required and/or the relative strength of the credentials required for that point on the continuum. As discussed below with reference to FIG. 4C, the continuum of authentication 400 may be coupled with a functions permitted continuum 400, first illustrated in FIG. 4B. In some embodiments, the confidence of the EEG reading comparison may allow for a hard authentication of the user into the authentication location based on a complete match between the baseline EEG reading and the EEG reading at the authentication location. In other embodiments, non-exact matches between the baseline EEG reading and the EEG reading at the authentication location provides a sliding scale from minimal credentials required or soft authentication up to the total match for hard authentication. The level of authentication required for each authentication location is determined by the location.

Referring to FIG. 4B, the functions permitted continuum 500 illustrates various levels of functions (e.g., electronic activities) permitted. Functions may refer to what a user is permitted to "see" and/or what the user is permitted to "do". More specifically, this may refer to whether a specific function is permitted at a certain point on the continuum and/or the context in which a certain function is permitted. The left-hand side of the continuum indicates that no functions are permitted, and the right-hand side of the continuum indicates that all functions are permitted. In between the extremes, minimal functions are permitted, moderate functions are permitted and most functions are permitted. Thus, any given point along the continuum 500 corresponds with a certain amount and/or number of functions that are permitted and/or the context in which certain functions are permitted. In some embodiments, the confidence of the EEG reading comparison may allow for all functions being permitted for the user into the authentication location based on a complete match between the baseline EEG reading and the EEG reading at the authentication location. In other embodiments, non-exact matches between the baseline EEG reading and the EEG reading at the authentication location provides a sliding scale from minimal functions up to the total match for all functions permitted.

Referring now to FIG. 4C, a diagram illustrates a coupling of the functions permitted continuum 500 and the levels of authentication continuum 400. As shown, the continua 500 and 400 may be coupled with one another such that the various points along the continua intersect at specific points of the coupled continuum based on confidence of an EEG reading match. For example, one continuum may be moved left or right with respect to the other continuum in order to achieve a different relationship between the functions permitted and the credentials required. Accordingly, for a given coupling, a specific point on continuum 500 provides that a particular function or functions may be permitted given that a specified level of confidence of the EEG match, as indicated by the corresponding point on continuum 400. For example, a financial institution and/or a user may arrange the continua 500 and 400 with respect to one another and may adjust the arrangement based on changing desires or goals.

In some embodiments, one or both the continua 500 and 400 may have weighted scales such that, as a point on the continuum is moved, the corresponding functions permitted and/or level of authentication required may change exponentially or otherwise based on a confidence level of the EEG match. Furthermore, in various embodiments, other representations of the various functions permitted that correspond with the various levels of authentication may be used by the invention. Furthermore, the level of authentication required to complete an electronic activity may be increased or decreased based on: (i) the collected device identification information for the local network devices associated with the previous electronic activities, (ii) the device identification information associated with the first computing device, and/or (iii) the device identification information associated with the local network devices in communication with the first local network.

Referring now to FIG. 4D, a diagram 600 illustrates a relationship between the functions permitted and the authentication types associated with the EEG reading match confidence. As shown in FIG. 4D, the soft authentication continuum between zero authentication and hard authentication may include one or more authentication types (A, B, C in the Figure). In one aspect, the one or more authentication types corresponding to the one or more levels of confidence associated with the EEG reading matching the user's EEG baseline reading. In one aspect, the EEG reading confidence level may correspond to authentication types A and B to perform moderate functions. In another aspect, the EEG reading confidence level may correspond to authentication types A, B, and C to perform most functions. In yet another aspect, the EEG reading confidence level may correspond to authentication type A to perform minimal functions.

As evident from the preceding description, the system described herein represents an improvement in technology by providing authentication levels and access to authentication locations using EEG patterning and confidence matching recognition. Accordingly, the system provides a technical solution for overcoming the problem of how to dynamically determine the level of authentication required for a particular electronic activity. Indeed, by automatically adjusting the level of required authentication based the identity of devices associated with an electronic activity, the likelihood of an unauthorized activity being performed can be reduced.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or having one or more application-specific circuits perform the function. As such, once the software and/or hardware of the claimed invention is implemented the computer device and application-specific circuits associated therewith are deemed specialized computer devices capable of improving technology associated with the in authentication and instant integration of a new credit card to digital wallets.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

It will further be understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions. These one or more computer-executable program code portions may be provided to a processor of a special purpose computer for the authentication and instant integration of credit cards to a digital wallet, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

INCORPORATION BY REFERENCE

To supplement the present disclosure, this application further incorporates entirely by reference the following commonly assigned patent applications:

| Docket Number | U.S. patent application Ser. No. | Title | Filed On |
| --- | --- | --- | --- |
| 8087US1.014033.3114 | To be assigned | ELECTROENCEPHALOGRAM TRIGGERED RESOURCE DISTRIBUTION QUERY SYSTEM | Concurrently herewith |
| 8088US1.014033.3115 | To be assigned | ELECTROENCEPHALOGRAM TRIGGERED EXPERIENCE MODIFICATION SYSTEM | Concurrently herewith |

What is claimed is:

1. A system for electroencephalogram (EEG) patterning recognition for authentication, the system comprising:
a memory device with computer-readable program code stored thereon;
a communication device;
a printing device for printing the resource distribution documents;
a processing device operatively coupled to the memory device and the communication device, wherein the processing device is configured to execute the computer-readable program code to:
identify a transmission from an EEG reader for establishing a baseline EEG reading for the user;
store the baseline EEG reading for the user in a EEG profile for the user, wherein the EEG profile comprises the baseline EEG reading for the user and authentication codes for one or more authentication locations;
identify the user requesting authentication into the one or more authentication locations;
locate an EEG reader at the one or more authentication locations and form a communicable linkage with the EEG reader at the one or more authentication locations;
receive an EEG reading from the EEG reader at the one or more authentication locations;
perform comparative spectral analysis to the EEG reading to identify a match or partial match to the baseline EEG reading for the user; and allow access into the one or more authentication locations based on a confidence of the comparative spectral analysis,
wherein allowing access into the one or more authentication locations based on a confidence of the comparative spectral analysis further comprises allowing access to functions of a portion of the authentication locations based on the confidence of a match of the EEG reading to the baseline EEG reading for the user to a hard authentication and an incomplete match of the EEG reading to the baseline EEG reading for the user to a soft authentication.

2. The system of claim 1, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

3. The system of claim 1, wherein receiving an EEG reading from the EEG reader at the one or more authentication locations, further comprises transmitting a request via the communicable linkage for generation of the EEG reading from the EEG reader at the one or more authentication locations.

4. The system of claim 1, wherein establishing a baseline EEG reading for the user further comprises transmitting one or more known stimuli to the user for EEG reading of user reaction to the known stimuli.

5. The system of claim 1, wherein performing comparative spectral analysis to the EEG reading to identify a match or partial match to the baseline EEG reading for the user further comprises generating a confidence that the EEG reading is an EEG reading of the user based on a comparative analysis to the baseline EEG reading for the user.

6. The system of claim 1, wherein one or more authentication locations comprise physical or digital locations requiring the user to authenticate to gain access to at least a portion of the physical or digital locations.

7. A computer program product for electroencephalogram (EEG) patterning recognition for authentication with at least one non-transitory computer-readable medium having computer-readable program code portions embodied therein, the computer-readable program code portions comprising:
an executable portion configured for integrating system application into receiving institution servers;
an executable portion configured for identifying a transmission from an EEG reader for establishing a baseline EEG reading for the user;
an executable portion configured for storing the baseline EEG reading for the user in a EEG profile for the user, wherein the EEG profile comprises the baseline EEG reading for the user and authentication codes for one or more authentication locations;
an executable portion configured for identifying the user requesting authentication into the one or more authentication locations;
an executable portion configured for locating an EEG reader at the one or more authentication locations and form a communicable linkage with the EEG reader at the one or more authentication locations;
an executable portion configured for receiving an EEG reading from the EEG reader at the one or more authentication locations;
an executable portion configured for performing comparative spectral analysis to the EEG reading to identify a match or partial match to the baseline EEG reading for the user; and
an executable portion configured for allowing access into the one or more authentication locations based on a confidence of the comparative spectral analysis,
wherein allowing access into the one or more authentication locations based on a confidence of the comparative spectral analysis further comprises allowing access to functions of a portion of the authentication locations based on the confidence of a match of the EEG reading to the baseline EEG reading for the user to a hard authentication and an incomplete match of the EEG reading to the baseline EEG reading for the user to a soft authentication.

8. The computer program product of claim 7, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

9. The computer program product of claim 7, wherein receiving an EEG reading from the EEG reader at the one or more authentication locations, further comprises transmitting a request via the communicable linkage for generation of the EEG reading from the EEG reader at the one or more authentication locations.

10. The computer program product of claim 7, wherein establishing a baseline EEG reading for the user further comprises transmitting one or more known stimuli to the user for EEG reading of user reaction to the known stimuli.

11. The computer program product of claim 7, wherein performing comparative spectral analysis to the EEG reading to identify a match or partial match to the baseline EEG reading for the user further comprises generating a confidence that the EEG reading is an EEG reading of the user based on a comparative analysis to the baseline EEG reading for the user.

12. The computer program product of claim 7, wherein one or more authentication locations comprise physical or digital locations requiring the user to authenticate to gain access to at least a portion of the physical or digital locations.

13. A computer-implemented method for electroencephalogram (EEG) patterning recognition for authentication, the method comprising:
providing a computing system comprising a computer processing device and a non-transitory computer readable medium, where the computer readable medium comprises configured computer program instruction code, such that when said instruction code is operated by said computer processing device, said computer processing device performs the following operations:
identifying a transmission from an EEG reader for establishing a baseline EEG reading for the user;
storing the baseline EEG reading for the user in a EEG profile for the user, wherein the EEG profile comprises the baseline EEG reading for the user and authentication codes for one or more authentication locations;
identifying the user requesting authentication into the one or more authentication locations;
locating an EEG reader at the one or more authentication locations and form a communicable linkage with the EEG reader at the one or more authentication locations;
receiving an EEG reading from the EEG reader at the one or more authentication locations;
performing comparative spectral analysis to the EEG reading to identify a match or partial match to the baseline EEG reading for the user; and
allowing access into the one or more authentication locations based on a confidence of the comparative spectral analysis,
wherein allowing access into the one or more authentication locations based on a confidence of the comparative spectral analysis further comprises allowing access to functions of a portion of the authentication locations based on the confidence of a match of the EEG reading to the baseline EEG reading for the user to a hard authentication and an incomplete match of the EEG reading to the baseline EEG reading for the user to a soft authentication.

14. The computer-implemented method of claim 13, wherein establishing a baseline EEG reading for the user further comprises compiling EEG data from the baseline EEG reading and performing spectral analysis to establish the baseline EEG reading, wherein spectral analysis comprises generating a cognitive event-related biometric recognition protocol for a late potential of the EEG reading.

15. The computer-implemented method of claim 13, wherein receiving an EEG reading from the EEG reader at the one or more authentication locations, further comprises transmitting a request via the communicable linkage for generation of the EEG reading from the EEG reader at the one or more authentication locations.

16. The computer-implemented method of claim 13, wherein establishing a baseline EEG reading for the user further comprises transmitting one or more known stimuli to the user for EEG reading of user reaction to the known stimuli.

17. The computer-implemented method of claim 13, wherein performing comparative spectral analysis to the EEG reading to identify a match or partial match to the baseline EEG reading for the user further comprises generating a confidence that the EEG reading is an EEG reading of the user based on a comparative analysis to the baseline EEG reading for the user.

* * * * *